United States Patent [19]

Everett

[11] Patent Number: 4,722,143
[45] Date of Patent: Feb. 2, 1988

[54] DISPOSABLE BOOT

[76] Inventor: Thomas W. Everett, 8270 West Point Dr., E. Amherst, N.Y. 14051

[21] Appl. No.: 3,297

[22] Filed: Jan. 14, 1987

[51] Int. Cl.⁴ .......................... A43B 3/16; A43B 1/02; A61F 13/00
[52] U.S. Cl. .................... 36/7.1 R; 36/9 R; 36/9 A; 2/239; 128/82
[58] Field of Search .......... 36/7.1 R, 7.2, 8.2, 36/9 A, 9 R, 10, 1.5, 2, 110; 2/239; 128/82

[56] References Cited

U.S. PATENT DOCUMENTS

| | | | |
|---|---|---|---|
| 1,884,284 | 10/1932 | Schneider | 36/7.1 R |
| 2,714,771 | 8/1955 | Olfene | 36/9 A |
| 4,562,834 | 1/1986 | Bates et al. | 128/82 |
| 4,599,812 | 7/1986 | Harmsen | 2/239 X |

FOREIGN PATENT DOCUMENTS

| | | | |
|---|---|---|---|
| 2373243 | 7/1978 | France | 36/9 R |
| 414247 | 7/1946 | Italy | 36/9 A |

*Primary Examiner*—James Kee Chi
*Attorney, Agent, or Firm*—Richard C. Litman

[57] ABSTRACT

A protective, disposable construction for covering an amputee's other limb while taking a cast of that limb for a prosthesis so the amputee's shoes, socks, slacks and proximate clothing do not become splashed with plaster during the cast taking process for maintaining a free and clean condition of the proximate clothing consisting of a pair of generally mirrored panels of material with sides and ends with a protuberance on one side at one end thereof and a stitch member disposed along the one side at the end adjacent the protuberance, the stitch member closing the one side and the end integrally together.

6 Claims, 3 Drawing Figures

U.S. Patent     Feb. 2, 1988     4,722,143

DISPOSABLE BOOT

BACKGROUND OF THE INVENTION

Field of the Invention

The invention relates to an improved disposable, protective boot used to protect the amputee's shoes, socks slacks, and the like, on a good limb from being splashed with plaster while taking a cast, the boot to be thrown out immediately after use and not to be used for any other purposes; and more particularly the invention is directed to a protective, disposable boot for covering an amputee's other limb while taking a cast of that limb for a prosthesis so the amputee's shoes, socks, slacks and proximate clothing do not become splashed with plaster during the cast taking process for maintaining a free and clean condition of the proximate clothing, the boot consisting of a pair of generally mirrored panels of material with sides and ends with a protuberance on one side at one end thereof, and a stitch member disposed along the one side at the end adjacent the protuberances, the stitch member closing the one side and the end integrally together.

The invention relates further to a device to be used strictly for the prosthetic and orthotic profession and the method of construction of the boot as more particularly described herein.

Description of the Prior Art

Various prior art disposable boot and covering devices, and the like, as well as apparatus and method of their construction in general, are found to be known and exemplary of the U.S. prior art are the following:

| | |
|---|---|
| 1,258,024 | Laybourn |
| 2,230,380 | Johst |
| 4,083,124 | Michalak |
| 4,335,527 | Pask |
| 4,598,485 | Joe et al |

Pask discloses a disposable boot having a sole, foot portion and leg segment. Laybourn is an overshoe of inexpensive fabric. Johst discloses a stocking and shoe protector of foldable material. Michalak and Joe et al show a disposable boot used to protect garments from plaster during making of a cast. The Joe et al patent also shows a disposable shoe cover worn by the doctor in the operating room, strictly for sanitary purposes.

These patents or known prior uses teach and disclose various types of disposable boot and covering devices of sorts and of various manufactures and the like as well as methods of their construction, but none of them whether taken singly or in combination disclose the specific details of the combination of the invention in such a way as to bear upon the claims of the present invention.

Summary of the Invention

An object, advantage and feature of the invention is to provide a novel boot device that is light-weight and compact in storage, and lends itself to economical and convenient packaging and dispensing.

Another object of the invention is directed further to a device providing for a boot that may be readily removed by the doctor and disposed after its use.

Also an object of the invention is to provide a simple and direct method for application of the boot to one's other limb while the foreshortened limb is being cast.

Another object of the invention is to provide a novel and improved method of construction of a boot for covering one's good limb during times of the foreshortened limb being cast for prosthetic purposes.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRTPTION OF THE SEVERAL VIEWS OF THE DRAWINGS

DESCRIPTION OF A PREFERRED EMBODIMEMT OF THE INVENTION

Figure 1:
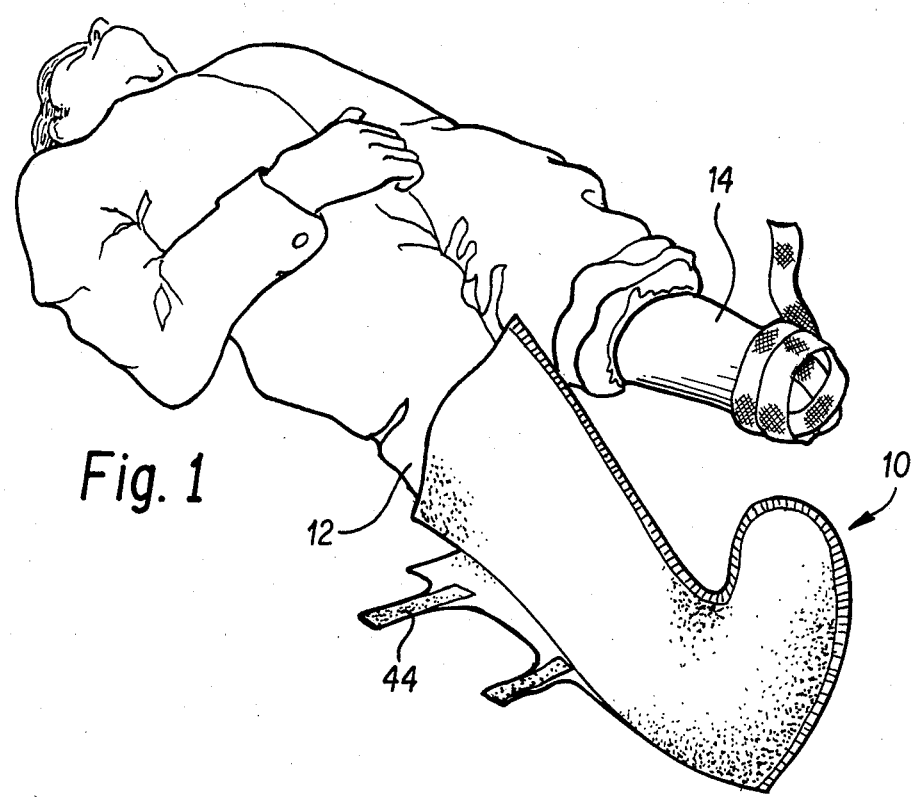
FIG. 1 is a perspective view of a patient in a reclining position and wearing the protective disposable boot according to a preferred embodiment and best mode of the present invention.
Figure 2:
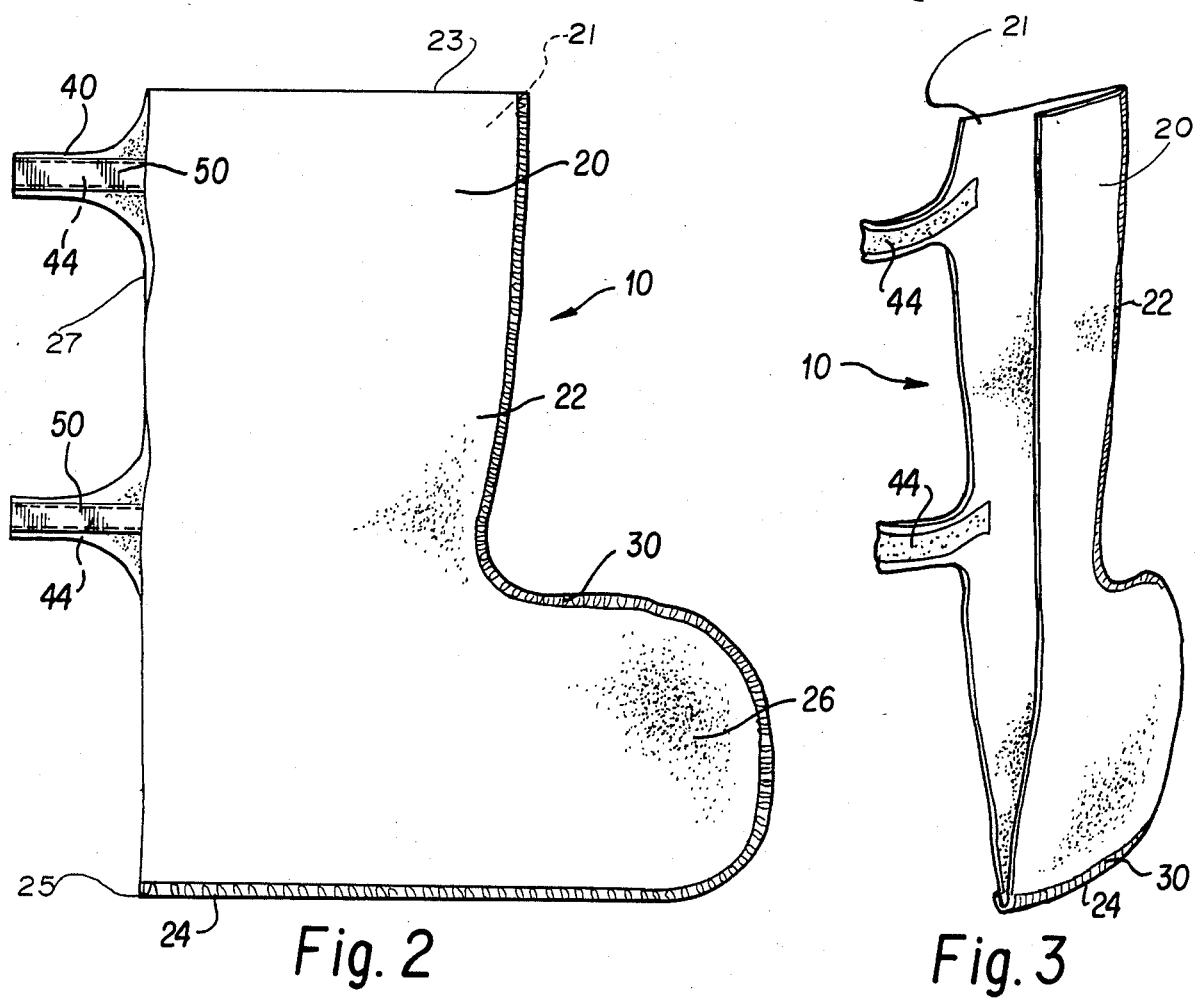
FIG. 2 is a side view of the disposable boot and adhesive strap and embodying the concepts of the invention.
Figure 3:
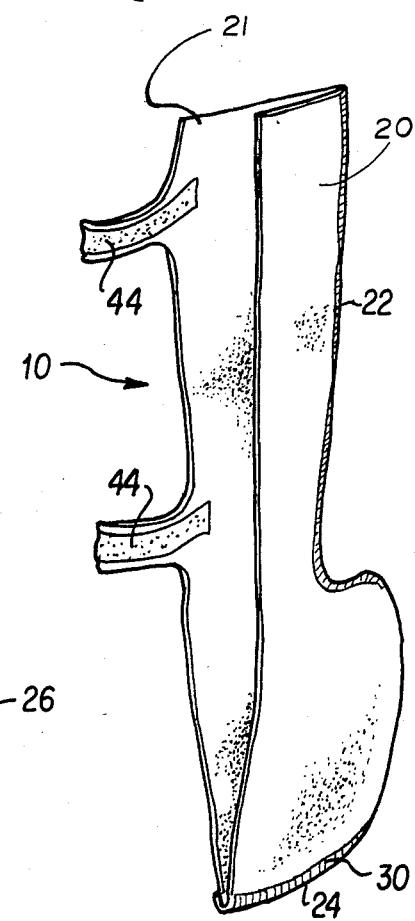
FIG. 3 is a rear pictorial view of the disposable boot showing an opening in the boot for insertion of the patient's foot and leg.

Referring now to the drawings there is shown in FIG. 1 a perspective view of a patient in a reclining position and wearing the protective disposable boot 10 consisting of a construction covering an amputee's other or good limb 12 while taking a cast of a foreshortened limb 14 for a prosthesis so an amputee's shoes, socks, slacks and proximate clothing on the other limb 12 do not become splashed with plaster during the cast taking process, and the amputee's clothing proximate to the casting may be maintained in a free and clean condition throughout the casting process. The boot 10 consists of a pair of generally mirrored panels comprising first and second panels 20,21 of material each with front edges 22, bottom edges 24 and a forward protuberance 26 forming a boot-shape of the boot 10 at the lower foot end thereof.

The panels 20,21 of the boot 10 are stitched by threads 30 disposed along the front edges 22, the protuberances 26 and the bottom edges 22 with the threads 30 closing the two panels integrally together as shown, from, the boot top edge 23 to the rear 25 of the bottom edge 24. The panels are preferably of absorbent paper material.

The panels 20,21 are provided with a plurality of integral tabs 40 extending rearwardly from the vertical rear edge 27 of the second panel 21. Adhesive strips 44 are provided on an inner facing side of the tabs 40 and these adhesive areas 44 have a protective facing or cover 50 thereon and removable from the adhesive areas 44 so the adhesive-provided tabs 40 may become securely adhered to an outer adjacent facing side of the other or first panel 20 for holding and maintaining the boot 10 in wrapped relation about the amputee's other limb 12 while the cast process is being taken of that portion of the amputee's foreshortened limb 14 for a prothesis. The panels are preferably dimensioned 17 by 33 inches such that the boot top edge 23 will be disposed above the patient's knee, as shown in FIG. 1. The material is a flexible material such as paper. The construction forming the boot 10 may be folded along a length or width dimension.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

What is claimed and desired to be secured by Letters Patent is:

1. A protective, disposable boot for covering a leg amputee's remaining limb while forming a cast of the adjacent missing limb for a prosthesis so the amputee's shoes, socks, slacks and proximate clothing on the remaining limb do not become splashed with plaster during the cast forming process, and maintaining a free and clean condition of the proximate clothing comprising:

first and second generally mirrored panels of material each hving a top edge and bottom edge, intermediate rear and front edges on said panels, said front edges provided with a forward protuberance adjacent said bottom edges, said top and bottom edges spaced apart a distance sufficient to extend between a user's foot and the top of their knee, stitch means fully and permanently joining said first and second panel front and bottom edges, a plurality of tabs integral with and projecting rearwardly from said rear edge of said second panel, a longitudinal strip of adhesive material on each said tab, a protective peelable cover overlying each said adhesive strip whereby, said boot may be applied to the remaining leg of an amputee disposed upon their back by placing the two panels over the top of the leg with the foot contained within said protuberance whereafter said two rear panel edges are fastened in an overlapping manner by removal of said protective covers and application of pressure upon said adhesive-provided tabs on said second panel against said first panel.

2. The apparatus of claim 1 wherein the panels are of absorbent paper material.

3. The apparatus of claim 1 wherein dimension of the panels are 17 by 33 inches.

4. The apparatus of claim 1 wherein the material is a flexible material.

5. The apparatus of claim 1 wherein the construction is folded along a length dimension.

6. The apparatus of claim 1 wherein the material is of paper.

* * * * *